United States Patent [19]

Chang

[11] 4,030,340

[45] June 21, 1977

[54] HYDROGEN GAS DETECTOR

[75] Inventor: Shih-Chia Chang, Santa Ana, Calif.

[73] Assignee: General Monitors, Inc., Costa Mesa, Calif.

[22] Filed: July 22, 1976

[21] Appl. No.: 707,678

[52] U.S. Cl. .................................. 73/23; 23/254 E; 338/34
[51] Int. Cl.² ........................................ G01N 27/04
[58] Field of Search ............ 73/23, 27 R; 23/254 E, 23/255 E; 324/65 R, 71 SN; 338/34; 340/237 R

[56] References Cited

UNITED STATES PATENTS

| 3,901,067 | 8/1975 | Boardman et al. | 73/23 |
| 3,952,567 | 4/1976 | Shinagaw et al. | 73/23 |

Primary Examiner—Herbert Goldstein
Attorney, Agent, or Firm—Lyon & Lyon

[57] ABSTRACT

A semiconductor article suitable for use in the detection of hydrogen gas in the atmosphere. The article comprises a film of palladium deposited onto a semiconductor film of stannic oxide which is positioned on a suitable substrate together with a resistance heating element. In some cases, the stannic oxide film is provided with a dopant to improve the operation of the article.

12 Claims, 3 Drawing Figures

HYDROGEN GAS DETECTOR

BACKGROUND OF THE INVENTION

This invention relates to a semiconductor article suitable for use in the detection of hydrogen gas in the atmosphere.

Because of the high combustibility of hydrogen, it is important that the presence of the gas be detected at relatively low concentrations on the order of 10 ppm. Although there are a number of analytical devcies which can accurately measure hydrogen at low concentrations, such equipment generally does not lend itself to field testing.

Hydrogen is often stored in large tanks or other containers situated in locations where the transportation of bulky analytical equipment is rendered impractical. Thus, the need for lightweight sensors, which can accurately detect the presence of hydrogen in the atomosphere at relatively low concentrations such as caused by a leak in the storage tank, has become apparent.

One prior lightweight sensor is disclosed in "Hydrogen Leak Detector Using a Pd-gate MOS Transistor," by L. Stiblert and C. Svensson, published in *Rev. Sci. Instrum.*, vol. 46, No. 9, September 1975. The device therein disclosed uses a conventional FET with the gate electrode comprised of palladium, and a temperature stabilizing circuit so the sensor can be operated at temperatures on the order of 150° C. The transistor comprises silicon and silicon dioxide. Also, a conventional FET device operates on the principleof electrostatic charge whereas the device of the present invention operates on a different mechanism, as discussed hereinafter.

It is therefore, an object of the present invention to provide a semiconductor article suitable for detecting the presence of low concentration of hydrogen in the atmosphere.

This and other objects and advantage are obtained by forming a thin film semiconductor article comprising a semiconductor detecting film having an activation film disposed thereon, a resistance means, and a thermistor. The semicondutor film principally comprises a thin layer of stannic oxide which may be doped with an impurity such as indium, to change the film conductivity. The semiconductor film is deposited onto one side of an inert refractory chip. A thermistor is also disposed onto this side of the chip. The resistance heating means is disposed onto this side of the chip. A thermistor is also disposed onto this side of the chip. The detecting film and the resistance heater are connected into separate, isolated circuits. The chip is then mounted onto an inorganic foam substrate.

DETAILED DESCRIPTION OF THE INVENTION

Figure 1:
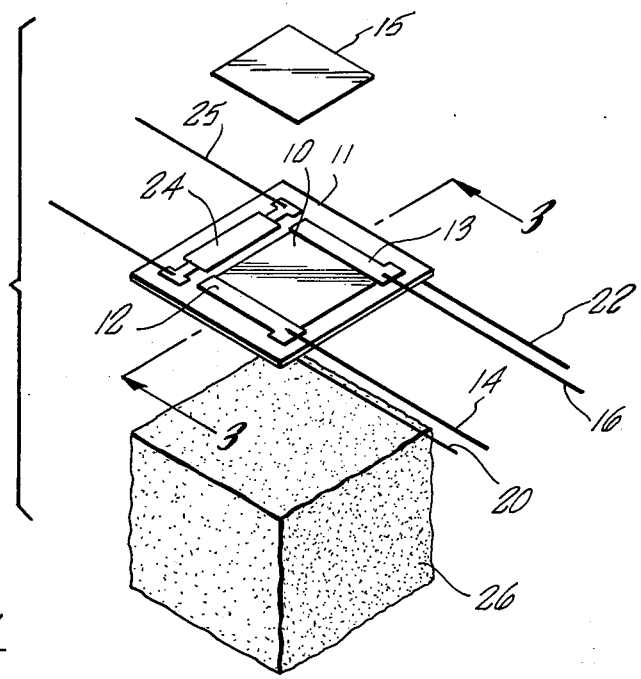
FIG. 1 is an exploded perspective view of the chip mounted onto the inorganic foam substrate.
Figure 3:
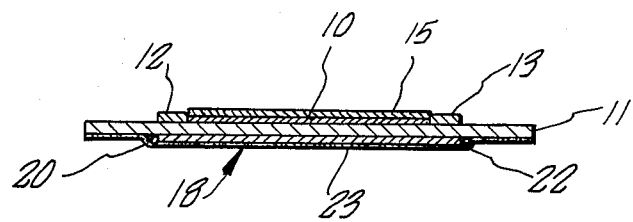
FIG. 3 is a cross-sectional view of FIG. 1 along line 3—3.

Referring to FIGS. 1 and 3, a semiconductor film 10 is desposited onto an inert refractory chip 11 between a pair of electrodes 12 and 13. The chip may be any suitable material which is stable at temperatures up to 200° C and to which the semiconductor film will adhere. Suitable materials include ceramics (e.g., steatite), glass, quartz, alumina or porcelain. The electrodes 12 and 13 are connected to leads 14 and 16 for measuring the conductance across film 10. The leads 14 and 16 are attached to any suitable conductivity measuring or sensing device (not shown). The electrodes and leads may be made of any suitable material, but preferably a noble metal such as platinum or gold is employed. The semiconductor film 10 is provided with hydrogen activation film 15 which is deposited onto film 10 between electrodes 14 and 16.

Figure 2:
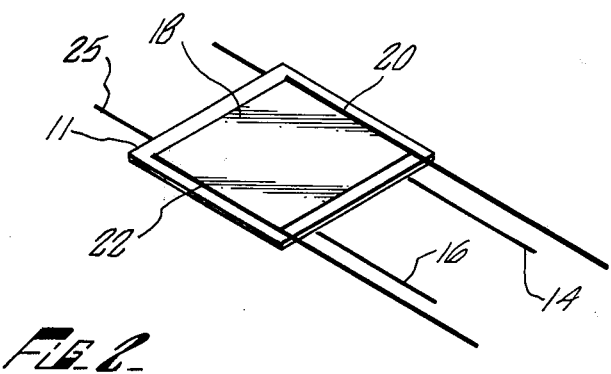
FIG. 2 is a bottom view of the chip onto which the resistance heater is disposed.

Referring to FIGS. 2 and 3, the bottom of the chip 11 is provided wth a resistance heating element 18 which functions to maintain the semiconductor film at a constant temperature above the ambient temperature, thereby reducing detection time as well as substantially eliminating detection errors caused by fluctuations in the ambient temperature. Thus, a wide range of constant temperatures is suitable. It is preferred that the temperature be maintained between approximately 100° C and 200° C and preferably approximately 170° C. Any suitable resistance heating element may be employed, such as a metallic film which may be deposited onto the chip 11 by any means well known in the art. The heating element 18 is provided with leads 20 and 22 which are preferably made of platinum or gold and are connected to any standard power source. The leads 20 and 22 are relatively thin, thereby preventing excessive heat transfer from the substrate to the support. The heater and leads are covered with a ceramic thick film insulator 23. The temperature of the heating element is controlled by a thermistor 24 positioned on the top of the chip. The thermistor is provided with leads 25 and is preferably covered with protective glass film (not shown).

Referring again to FIG. 1, it may be seen that, if desired, the chip 11 may be mounted on an inorganic foam substrate 26 such as talc. The inorganic substrate functions to support the chip without acting as a heat sink. The chip is mounted onto the substrate 26 so that the resistance heater 18 is adjacent the substrate and the insulator 23 is disposed between the chip and the substrate. The chip is preferably glued onto the substrate to permanently mount it thereon.

The semiconductor thin film 10 is preferably deposited onto the substrate by sputtering. However, other conventional techniques such as evaporation or solution coating may also be utilized. The film is preferably deposited only between the two electrodes 12 and 13. The film is preferably comprised of stannic oxide but, in some cases, dopant may also be desired. Indium is preferred as a dopant; however, other dopants which may be employed include zinc, cadmium, aluminum, gallium, tellurium, arsenic, antimony, bismuth, or palladium. Selection of the type and concentration of dopant will depend upon the initial conductivity of the film desired, the change in conductivity desired after exposure to certain levels of hydrogen, and the rate in conductivity needed.

The thickness of the deposited film may range from 4000A to 10,000A, depending upon the resistance needed. However, thinner films are generally preferred because the thinner the film, the lower the initial conductivity. Sputtering is generally the preferred method of depositing the detecting film onto the chip.

The semiconductor film 10 is provided with an activation film 15, which is preferably disposed over the entire surface of the semiconductor film. The film 15 may be comprised of palladium, or palladium-gold alloy consisting of perferably approximately 40% palladium and 60% gold. The film 15 is preferably desposited onto the smeiconductor film by evaporation. In FIG. 1, the film 15 is shown symbolically for ease of understanding as a continuous sheet. However, the film 15 is preferably formed as a myriad of discrete islands of the palladium over the entire semiconductor film. The discrete islands function to prevent the electrodes from shorting out. The film is formed of a thickness of approximately 30–70A, and preferably 50A although, in some cases, other thicknesses may be suitable. At a film thickness of approximately 30–70A, the islands are noncontinuous. However, at greater thicknesses, the islands may become continuous, thereby shorting out the device.

Although the operation of the device is not entirely understood, it is believed that the stannic oxide of semiconductor film 10 contains chemisorbed oxygen which withdraws electron density from the conduction band of the film 10. When the device is exposed to hydrogen, the diatomic hydrogen molecules are activated or dissociated by the palladium film 15 to form hydrogen atoms. The hydrogen atoms then react with the chemisorbed oxygen to form minute amounts of water and release electron density into the conduction band of the semiconductor film 10. It is also believed that the hydrogen supplies an extra electron to the conduction band of the semiconductor film 10 which also increases the conductivity of the semiconductor film 10.

In operation, the leads 14 and 16 are connected directly to a suitable conductivity measuring device to enable the measurement of the conductance across film 10. The leads 20 and 22 are connected directly to a suitable electrical power source to enable heating of the heating element 18. Since the detecting circuit and the heating circuit are isolated, the measuring device does not experience interference or false readings from the heating circuit. The semiconductor article is then heated to an elevated temperature of about 170° C in a hydrogen-free atmosphere. The resistance across the film is then measured from electrode 12 to electrode 13. The sensor is then placed in contact wth the gaseous sample to be tested and a final conductivity measurement is taken. At lower concentration on the order of 1 ppm, the final measurement is preferably taken after approximately 6 to 10 minutes exposure to the gaseous atmosphere. However, at higher concentrations on the order of 20 ppm, the final measurement may be taken after about one minute. From the change in conductivity, the amount of hydrogen present is determined. Alternatively, through the use of more sophisticated equipment known to those skilled in the art, the rate of change in conductivity may be measured, thereby giving even faster results.

While an embodiment and application of this invention has been shown and described, it will be apparent to those skilled in the art that many more modifications are possible without departing from the inventive concepts herein described. The invention, therefore, is to be limited only by the lawful scope of the claims which follow.

What is claimed is:

1. An article for detecting the concentration of hydrogen in the atmosphere, comprising:
   a semiconductor detecting film comprising stannic oxide and deposited onto an inert substrate;
   electrode means connected to said film; and a hydrogen activation film deposited onto said semiconductor detecting film.

2. An article according to claim 1 wherein said article is further provided with a resistance heater disposed onto said substrate.

3. An article according to claim 2 wherein said substrate is also provided with a temperature sensing means for controlling said resistance heater to maintain said substrate at a constant temperature.

4. The article according to claim 3 wherein said sensing means is a thermistor.

5. An article according to claim 1 wherein said oxide is provided with a dopant selected from the group consisting of zinc, cadmium, aluminum, gallium, indium, tellurium, arsenic, antimony, bismuth or palladium.

6. An article according to claim 5 wherein said dopant is indium.

7. An article according to claim 5 wherein said dopant is aluminum.

8. An article according to claim 1 wherein said activation film is comprised of a material selected from the group consisting of palladium and palladium-gold alloy.

9. An article according to claim 1 wherein said activation film is comprised of palladium.

10. An article according to claim 9 wherein said palladium film has a thickness of between approximately 30–70A.

11. An article according to claim 10 wherein the thickness of said palladium film is approximately 50A.

12. An article for detecting the concentration of hydrogen in the atmosphere comprising:
   a resistance heater disposed onto an inert, refractory chip;
   a semiconductor detecting film deposited onto said chip and comprised of stannic oxide and a dopant selected from the group consisting of zinc, cadmium, aluminum, gallium, indium, tellurium, arsenic, antimony, bismuth or palladium, said detecting film havng a separate electrical circuit from said resistance heater; and
   an activation film deposited onto said semiconductor detecting film and comprised of a material selected from the group consisting of palladium and palladium-gold alloy.

* * * * *